(12) United States Patent
Smith

(10) Patent No.: US 8,263,563 B2
(45) Date of Patent: Sep. 11, 2012

(54) FURIN INHIBITORS

(75) Inventor: Robert E. Smith, Livermore, CA (US);
Judith Smith, legal representative,
Livermore, CA (US)

(73) Assignees: Robert E. Smith, Cominskey, IN (US);
Judith Smith, Comiskey, IN (US)

( * ) Notice: Subject to any disclaimer, the term of this patent is extended or adjusted under 35 U.S.C. 154(b) by 942 days.

(21) Appl. No.: 11/572,399

(22) PCT Filed: Jul. 22, 2005

(86) PCT No.: PCT/US2005/026086
§ 371 (c)(1),
(2), (4) Date: Nov. 14, 2008

(87) PCT Pub. No.: WO2007/046781
PCT Pub. Date: Apr. 26, 2007

(65) Prior Publication Data
US 2009/0131328 A1    May 21, 2009

Related U.S. Application Data

(60) Provisional application No. 60/590,577, filed on Jul. 23, 2004.

(51) Int. Cl.
*A61K 38/08* (2006.01)
(52) U.S. Cl. .................................................. 514/21.8
(58) Field of Classification Search .................. None
See application file for complete search history.

(56) References Cited

U.S. PATENT DOCUMENTS

| | | | |
|---|---|---|---|
| 5,604,201 | A | 2/1997 | Thomas et al. |
| 6,022,855 | A | 2/2000 | Thomas et al. |
| 6,180,356 | B1 | 1/2001 | London et al. |
| 6,210,929 | B1 | 4/2001 | Schlokat et al. |
| 6,272,365 | B1 | 8/2001 | Ronkainen et al. |
| 6,274,365 | B1 | 8/2001 | Van de ven et al. |
| 6,596,526 | B1 | 7/2003 | Plaimauer et al. |
| 2003/0087827 | A1 | 5/2003 | Lindberg et al. |

FOREIGN PATENT DOCUMENTS

| EP | 0678121 B1 | 6/2003 |
|---|---|---|
| WO | WO-91/08314 | 5/1991 |

OTHER PUBLICATIONS

Hatanaka, Y. et al., "Interactions of Derivatives of Guanidinophenylalanine and Guanidinophenylglycine with Streptomyces Griseus Trypsin" Biochemica Et Biophysica ACTA. Protein Structure and Molecular ENzymology, Elsevier, Amsterdam; vol. 832, No. 3, Dec. 20, 1985, pp. 274-279.

Jean, F. et al., "Fluorescent peptidyl substrates as an aid in studying the substrate specificity of human prohormone convertase PC1 and human furin and designing a potent irreversible inhibitor." The Journal of Biological Chemistry Aug. 18, 1995, vol. 270, No. 33, pp. 19225-19231.

Stieneke-Groeber, A. et al., "Influenza Virus Hemagglutinin with Multibasic Cleavage Site is Activated by Furin, A Subtillisin-Like Endoprotease" EMBO Journal, Oxford University Press, vol. 11, No. 7, Jan. 1, 1992, pp. 2407-2414.

Supplemental European Search Report Issued on May 10, 2010 in Application No. 0585853.7-2404/1799244 PCT/US2005026086.

Bahbouhi, B. et al., "Inhibition of HIV-2 ROD Replication in a Lymphobastoid Cell Line by the al-antitrypsin Portland variant (al - PDX) and the decRVKRcmk peptide:comparison with HIV-1 LAI" Microbes and Infection, vol. 3 (2001), pp. 1073-1084.

Carmeron, A., Appel, Jon.,Houghten, R.A., and Lindberg, I., "Polyarginines are Potent Furin Inhibitors" The Journal of Biological Chemistry, vol. 275, No. 47 (Nov. 24, 2000) pp. 36741-36749.

Flower, J. R., et al., "Analgesic-Antipyretics and Anti-Inflammatory Agents; Drugs Employed in the Treatment of Gout." in Gillman, Goodman and Gilman., The Pharmacological Basis of Therapeutics, 6th Ed. (New York, Macmillan Publishing Co., Inc. 1980), pp. 682-728.

Hallenberger, S., Bosch, V., Angliker,H., Shaw, E., Klenk, H.D., Garten, W., "Inhibition of furin-mediated cleavage activation of HIV-1 glycoprotein gp160" Letters to Nature, vol. 360 (Nov. 26, 1992) pp. 358-361.

Messageot, F. et al., "Proteolytic Processing of Hepatitis B Virus e Antigen Precursor." J. Biol. Chem., vol. 278, Issue 2 (Jan. 10, 2003).

Panchal, R. et al., "Identification of Small Molecule Inhibitors of Anthrax Lethal Factor" Nature Structural & Molecular Biology, vol. 11, No. 1 (Jan. 2004), pp. 67-72.

Sarac, M.S., et al.," Protection Against Anthrax Toxemia by Hexa-D-Arginine in Vitro and in Vivo" Infection and Immunity, vol. 72, No. 1(Jan. 2004), pp. 602-605.

Thomas, G. "Furin at the Cutting Edge: From Protein Traffic to Embryogenesis and Disease" Nature Reviews/Molecular Cell Biology, vol. 3 (Oct. 2002). pp. 753-766.

*Primary Examiner* — Christina Bradley

(74) *Attorney, Agent, or Firm* — Woodard, Emhardt, Moriarty, McNett & Henry LLP

(57) ABSTRACT

Inhibitors for the endoprotease furin are provided for the prevention, diagnosis, treatment, and study of human and animal pathologies, which involve furin activity. These pathologies include infections caused by bacteria and virus that exploit host furin activity. These pathologies also include diseases that involve the expression of host proproteins that are processed by furin as a part of growth, development, and maintenance of the host organism including certain cancers of the head and neck.

1 Claim, 8 Drawing Sheets

SEQUENCE LISTING

<160> NUMBER OF SEQ ID NOS: 27

<210> SEQ ID NO 1
<211> LENGTH: 794
<212> TYPE: PRT
<213> ORGANISM: Homo sapien

<400> SEQUENCE: 1

```
Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp Ala Val Arg Ile Pro Gly Gly Pro Ala Val Ala Asn Ser Val
        35                  40                  45

Ala Arg Lys His Gly Phe Leu Asn Leu Gly Gln Ile Phe Gly Asp Tyr
    50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
        195                 200                 205

Gly Val Cys Gly Val Gly Val Ala Tyr Asn Ala Arg Ile Gly Gly Val
    210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
            260                 265                 270

Ala Phe Phe Arg Gly Val Ser Gln Gly Arg Gly Gly Leu Gly Ser Ile
        275                 280                 285

Phe Val Trp Ala Ser Gly Asn Gly Gly Arg Glu His Asp Ser Cys Asn
    290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
                325                 330                 335

Leu Ala Thr Thr Tyr Ser Ser Gly Asn Gln Asn Glu Lys Gln Ile Val
            340                 345                 350
```

-continued

Thr Thr Asp Leu Arg Gln Lys Cys Thr Glu Ser His Thr Gly Thr Ser
        355                 360                 365

Ala Ser Ala Pro Leu Ala Ala Gly Ile Ile Ala Leu Thr Leu Glu Ala
        370                 375                 380

Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
                405                 410                 415

Gly Arg Lys Val Ser His Ser Tyr Gly Tyr Gly Leu Leu Asp Ala Gly
                420                 425                 430

Ala Met Val Ala Leu Ala Gln Asn Trp Thr Thr Val Ala Pro Gln Arg
            435                 440                 445

Lys Cys Ile Ile Asp Ile Leu Thr Glu Pro Lys Asp Ile Gly Lys Arg
        450                 455                 460

Leu Glu Val Arg Lys Thr Val Thr Ala Cys Leu Gly Glu Pro Asn His
465                 470                 475                 480

Ile Thr Arg Leu Glu His Ala Gln Ala Arg Leu Thr Leu Ser Tyr Asn
                485                 490                 495

Arg Arg Gly Asp Leu Ala Ile His Leu Val Ser Pro Met Gly Thr Arg
                500                 505                 510

Ser Thr Leu Leu Ala Ala Arg Pro His Asp Tyr Ser Ala Asp Gly Phe
        515                 520                 525

Asn Asp Trp Ala Phe Met Thr Thr His Ser Trp Asp Glu Asp Pro Ser
        530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
                565                 570                 575

Gly Leu Pro Val Pro Pro Glu Ser Ser Gly Cys Lys Thr Leu Thr Ser
            580                 585                 590

Ser Gln Ala Cys Val Val Cys Glu Glu Gly Phe Ser Leu His Gln Lys
        595                 600                 605

Ser Cys Val Gln His Cys Pro Pro Gly Phe Ala Pro Gln Val Leu Asp
        610                 615                 620

Thr His Tyr Ser Thr Glu Asn Asp Val Glu Thr Ile Arg Ala Ser Val
625                 630                 635                 640

Cys Ala Pro Cys His Ala Ser Cys Ala Thr Cys Gln Gly Pro Ala Leu
                645                 650                 655

Thr Asp Cys Leu Ser Cys Pro Ser His Ala Ser Leu Asp Pro Val Glu
            660                 665                 670

Gln Thr Cys Ser Arg Gln Ser Gln Ser Ser Arg Glu Ser Pro Pro Gln
        675                 680                 685

Gln Gln Pro Pro Arg Leu Pro Pro Glu Val Glu Ala Gly Gln Arg Leu
        690                 695                 700

Arg Ala Gly Leu Leu Pro Ser His Leu Pro Glu Val Val Ala Gly Leu
705                 710                 715                 720

Ser Cys Ala Phe Ile Val Leu Val Phe Val Thr Val Phe Leu Val Leu
                725                 730                 735

Gln Leu Arg Ser Gly Phe Ser Phe Arg Gly Val Lys Val Tyr Thr Met
            740                 745                 750

Asp Arg Gly Leu Ile Ser Tyr Lys Gly Leu Pro Pro Glu Ala Trp Gln
            755                 760                 765

```
Glu Glu Cys Pro Ser Asp Ser Glu Glu Asp Glu Gly Arg Gly Glu Arg
        770                 775                 780

Thr Ala Phe Ile Lys Asp Gln Ser Ala Leu
785                 790

<210> SEQ ID NO 2
<211> LENGTH: 5
<212> TYPE: PRT
<213> ORGANISM: Artificial Sequence
<220> FEATURE:
<223> OTHER INFORMATION: peptide portion of a furin inhibitor

<400> SEQUENCE: 2

Glu Arg Val Arg Arg
1               5

<210> SEQ ID NO 3
<211> LENGTH: 5
<212> TYPE: PRT
<213> ORGANISM: Artificial Sequence
<220> FEATURE:
<223> OTHER INFORMATION: peptide portion of a furin inhibitor

<400> SEQUENCE: 3

Arg Val Arg Arg Arg
1               5

<210> SEQ ID NO 4
<211> LENGTH: 7
<212> TYPE: PRT
<213> ORGANISM: Bacillus anthrasis

<400> SEQUENCE: 4

Asn Ser Arg Lys Lys Arg Ser
1               5

<210> SEQ ID NO 5
<211> LENGTH: 7
<212> TYPE: PRT
<213> ORGANISM: Costridium septicum

<400> SEQUENCE: 5

Lys Arg Arg Gly Arg Arg Ser
1               5

<210> SEQ ID NO 6
<211> LENGTH: 7
<212> TYPE: PRT
<213> ORGANISM: Corynebacterium diptheriae

<400> SEQUENCE: 6

Gly Asn Arg Val Arg Arg Ser
1               5

<210> SEQ ID NO 7
<211> LENGTH: 7
<212> TYPE: PRT
<213> ORGANISM: Aeromonas hydrophila

<400> SEQUENCE: 7

Lys Val Arg Arg Ala Arg Ser
1               5
```

```
<210> SEQ ID NO 8
<211> LENGTH: 7
<212> TYPE: PRT
<213> ORGANISM: Pseudomonas aeruginosa

<400> SEQUENCE: 8

Arg His Arg Gln Pro Arg Gly
1               5

<210> SEQ ID NO 9
<211> LENGTH: 7
<212> TYPE: PRT
<213> ORGANISM: Shigella dysenteriae

<400> SEQUENCE: 9

Ala Ser Arg Val Ala Arg Met
1               5

<210> SEQ ID NO 10
<211> LENGTH: 7
<212> TYPE: PRT
<213> ORGANISM: Avian Influenza HA

<400> SEQUENCE: 10

Arg Arg Arg Lys Lys Arg Gly
1               5

<210> SEQ ID NO 11
<211> LENGTH: 7
<212> TYPE: PRT
<213> ORGANISM: Borna Disease Virus

<400> SEQUENCE: 11

Leu Lys Arg Arg Arg Arg Asp
1               5

<210> SEQ ID NO 12
<211> LENGTH: 7
<212> TYPE: PRT
<213> ORGANISM: Cytomegalovirus

<400> SEQUENCE: 12

Thr His Arg Thr Arg Arg Ser
1               5

<210> SEQ ID NO 13
<211> LENGTH: 7
<212> TYPE: PRT
<213> ORGANISM: Ebola Zaire

<400> SEQUENCE: 13

Gly Arg Arg Thr Arg Arg Glu
1               5

<210> SEQ ID NO 14
<211> LENGTH: 7
<212> TYPE: PRT
<213> ORGANISM: Marburg Virus

<400> SEQUENCE: 14

Val Tyr Arg Arg Lys Arg Ser
1               5
```

```
<210> SEQ ID NO 15
<211> LENGTH: 7
<212> TYPE: PRT
<213> ORGANISM: Epstein-Barr virus

<400> SEQUENCE: 15

Leu Arg Arg Arg Arg Arg Asp
1               5

<210> SEQ ID NO 16
<211> LENGTH: 7
<212> TYPE: PRT
<213> ORGANISM: Human immunodeficiency virus

<400> SEQUENCE: 16

Val Gln Arg Glu Lys Arg Ala
1               5

<210> SEQ ID NO 17
<211> LENGTH: 7
<212> TYPE: PRT
<213> ORGANISM: Infectious Bronchitis virus

<400> SEQUENCE: 17

Thr Arg Arg Phe Arg Arg Ser
1               5

<210> SEQ ID NO 18
<211> LENGTH: 7
<212> TYPE: PRT
<213> ORGANISM: Japanese B encephalitis

<400> SEQUENCE: 18

Ser Lys Arg Ser Arg Arg Ser
1               5

<210> SEQ ID NO 19
<211> LENGTH: 7
<212> TYPE: PRT
<213> ORGANISM: Measles virus

<400> SEQUENCE: 19

Ser Arg Arg His Lys Arg Phe
1               5

<210> SEQ ID NO 20
<211> LENGTH: 7
<212> TYPE: PRT
<213> ORGANISM: Mumps

<400> SEQUENCE: 20

Ser Arg Arg His Lys Arg Phe
1               5

<210> SEQ ID NO 21
<211> LENGTH: 7
<212> TYPE: PRT
<213> ORGANISM: Respitory-syncitial virus

<400> SEQUENCE: 21

Lys Lys Arg Lys Arg Arg Phe
1               5
```

```
<210> SEQ ID NO 22
<211> LENGTH: 7
<212> TYPE: PRT
<213> ORGANISM: Rous sarcoma virus

<400> SEQUENCE: 22

Gly Ile Arg Arg Lys Arg Ser
1               5

<210> SEQ ID NO 23
<211> LENGTH: 7
<212> TYPE: PRT
<213> ORGANISM: Yellow Fever Virus

<400> SEQUENCE: 23

Ser Lys Arg Ser Arg Arg Ser
1               5

<210> SEQ ID NO 24
<211> LENGTH: 5
<212> TYPE: PRT
<213> ORGANISM: Arbovirus

<400> SEQUENCE: 24

Arg Ser Arg Arg Ser
1               5

<210> SEQ ID NO 25
<211> LENGTH: 5
<212> TYPE: PRT
<213> ORGANISM: Coronavirus

<400> SEQUENCE: 25

Arg Lys Arg Arg Ser
1               5

<210> SEQ ID NO 26
<211> LENGTH: 7
<212> TYPE: PRT
<213> ORGANISM: Vacinnia virus

<400> SEQUENCE: 26

Gly Ile Arg Ala Arg Arg Ser
1               5

<210> SEQ ID NO 27
<211> LENGTH: 4
<212> TYPE: PRT
<213> ORGANISM: Artificial Sequence
<220> FEATURE:
<223> OTHER INFORMATION: peptide portion of furin inhibitor

<400> SEQUENCE: 27

Arg Val Lys Arg
1
```

US 8,263,563 B2

FURIN INHIBITORS

CROSS-REFERENCE TO RELATED APPLICATIONS

This application is a national-stage application of Patent Application Ser. No. PCT/US2005/028068 filed Jul. 22, 2005, which claims the benefit U.S. Provisional Patent Application Ser. No. 60/590,577 filed Jul. 23, 2004, both of which are incorporated herein by reference in their entirety.

GOVERNMENT LICENSE RIGHTS

The testing of this invention was supported in part by the United States Government under National Institute of Health Grant No. DK37274. Accordingly, the government has certain rights in the invention.

TECHNICAL FIELD OF THE INVENTION

The present invention relates to compounds that modulate furin activity and methods of using these compounds in the prevention, treatment, diagnosis, and study of diseases that affect humans and animals.

BACKGROUND OF THE INVENTION

Most proteins produced by eukaryotic organisms are produced as larger proproteins that are generally either less active, or entirely inactive. Many proproteins are processed in transit through the secretory pathway of the Golgi apparatus where specific proteases cleave peptide bonds at specific amino acid sequences to produce functionally mature proteins. Still other propeptides are first transported to specific regions of the cell or the cell membrane where they are cleaved at specific amino acid sequences to produce mature proteins.

Proteins first produced as larger propeptides then cleaved into more functional polypeptides include but are not limited to serum albumin, cell surface receptors, adhesion molecules, peptide hormones such as pro-insulin, neuropeptides, growth factors, and components of the clotting cascade.

One especially widespread and indispensable protease active in both the secretory pathway and on, or near the cell surface, is the endoprotease furin. Furin, is itself produced as a proprotein (SEQ ID NO. 1), cycles between the Golgi apparatus, endosomes, and cell membrane. Furin is active in both embryogenesis and in mature cells. At steady state, furin is localized principally in the trans-Golgi network (TGN)/Endosomal system. Depending upon its location in the system, furin catalyses a number of different reactions, all involving proteolytic cleavage of proproteins. For example, in the TGN/biosynthetic pathway furin cleaves a propeptide to give active pro-β nerve growth factor (pro-β-NGF). Similarly, furin cleaves propeptides thereby activating pro-bone morphogenic protein-4 (pro-BMP-4) and the "single-chain" insulin pro-hormone to form the higher activity latter-form entity.

A number of pathogens also exploit host cell furin activity to help activate proteins involved in pathology. For example host cell furin cleaves the Ebola Zaire pro-glycoprotein (pro-GP) protein as part of the virus's infectious cycle. Furin located in the host cell membrane cleaves proproteins produced by bacterial pathogens to create active forms of the bacterial proteins such as anthrax protective antigen (PA), and *Clostridium septicum* α-toxin. Additionally, furin in the early endosome, cleaves propeptides to produce active bacterial proteins such as diptheria toxins, shigala toxin, shigala-like toxin 1, and *Pseudomonas* exotoxin A. Furin processes the coat protein of Human Immunodeficiency Virus (HIV) and PA toxin produced by *Bacillus anthrasis*. For a more through discussion of furins and furin activity, the reader is directed to "Furin at the Cutting Edge: From Protein Traffic to Embryogenesis and Disease" Gary Thomas, *Nature Reviews Molecular Cell Biology* Vol. 3, October 2002 pg. 753-766, which is hereby incorporated by reference in its entirety.

In addition to the propeptides already discussed furin and other subtilins-like proteases, also cleave proproteins that produce active forms of hormones and growth factors (e.g., proactivin A, hepatocyte-growth factor), plasma proteins (albumin, factor VII, factor IX, factor X), receptors (insulin pro-receptor). Additional pathogen derived propeptides processed by furin and other subtilins-like proteases include, for example, viral proteins such as HIV-1 coat protein gp160, and influenza virus hemagglutinin as well as bacterial proteins such as diphtheria toxin, and anthrax toxin. For further discussion of the role of furins in cellular metabolism and pathology the reader is directed to the following references all of which are hereby incorporated by reference in their entirety, (Decroly et al., J. Biol. Chem. 269:12240-12247, 1994, Stieneke-Grober et al., EMBO J. 11:2407-2414, 1992, Barr, Cell 66:1-3, 1991, Wasley et al., J. Biol. Chem. 268:8458-8465, 1993, Klimpel et al., Proc. Natl. Acad. Sci. USA 89:10277-10281, 1992, Tsuneoka et al., J. Biol. Chem. 268: 26461-26465, 1993, Bresnahan et al., J. Cell. Biol. 111:2851-2859, 1990, Hosaka et al., J. Biol. Chem. 266:12127-12130, 1991, Vey et al., J. Cell. Biol. 127:1829-1842, 1994.

Because of furin's importance in both cellular development and maintenance and its role in pathology, furin has become the focus of considerable study. This interest has resulted in the development of some furin inhibitors useful in the study of furin activity and in the treatment of diseases that involve furin activity. Currently available furin inhibitors include the furin propeptide itself (SEQ ID NO. 1), specific alkylating agents, a polypeptide consisting of L-arginines, and polypeptide derivatives of $\alpha_1$-antitrypsin. For further discussion of furin inhibitors the reader is directed to: U.S. Pat. No. 6,022,855; "Polyarginines Are Potent Furin Inhibitors" A. Cameron, J. Appel, R. A. Houghten, and I. Lindberg, *The Journal of Biological Chemistry*, Vol. 275, No. November 24, pg. 36741-36749; and U.S. patent application publication No. 2003/0087827, all of which are herein incorporated by reference in their entirety.

A typical Furin propeptide is described in U.S. Pat. No. 6,272,365 B1. The typical sequence representative of a human furin propeptide (SEQ ID. No. 1 submitted by K. Strausberg, et al. (gi: 15082544) is available from the National Center for Biotechnology Information (NCBI).

Other alkylating agents such as ketomethylene and octapeptidyl chloromethane derivatives are effective inhibitors of furin, unfortunately they are too toxic to be of general therapeutic value. For a further discussion of these reagents the reader is directed to see, for example, S. Jallenberger, et al., *Nature* 1992, pp 358-361, vol. 360, which is herein incorporated by reference in its entirety.

The $\alpha_1$-antitrypsin derivatives used as furin inhibitors are less toxic to eukaryotic host cells than are the currently used alkylating agents. However, $\alpha_1$-antitrypsin derivatives are large polypeptides, not readily taken up by cells. The most practical means of delivering $\alpha_1$-antitrypsin derivative furin inhibitors is by gene therapy. This delivery system includes all of the complications and risks generally associated with gene therapy.

Although the general association between specific disease states and furin activity is known, it is unlikely that all disease states associated with furin activity have been discovered. Because of the essential role furin plays in metabolism, development, and a wide variety of pathologies there is an urgent need for compounds and methods for regulating furin activity. It is one object of the invention to provide such compounds and methods.

SUMMARY OF THE INVENTION

Briefly describing the present invention, there is provided compounds and methods for diagnosing, preventing, and treating medical conditions involving furin activity. In one embodiment compounds and methods are used to diagnose, prevent, and treat diseases involving furin activity.

One embodiment comprises an n-mer or a pharmaceutically acceptable salt thereof, of a compound with the formula:

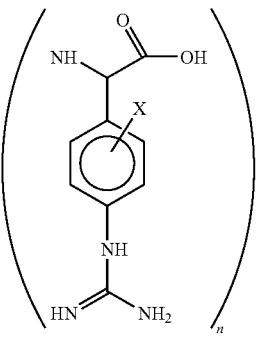

[Compound 1]

wherein,
the n-mer is a polypeptide comprised of the D-enantiomers of the compounds illustrated in FIG. 1 joined by peptide bonds,
n is greater than or equal to 1 and less than or equal to 6; and
X is either hydrogen (H) or fluorine (F).

One embodiment comprises a hexamer of the D-enantiomers of the compound illustrated in FIG. 1, having the following formula or a pharmaceutically acceptable salt thereof:

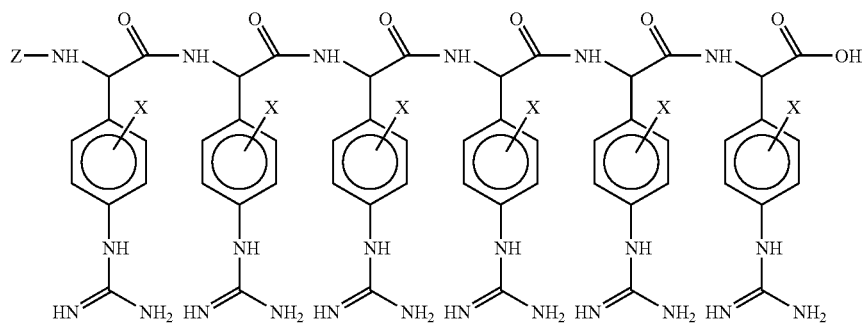

[Compound 2]

wherein,
X is either hydrogen, fluorine or a combination thereof; and
Z is Hydrogen or an N-terminal blocking group selected from the group comprising α-lipoic acid, pyroglutamic acid, 4-morpholinylcaronyl, CBZ, or a derivative of propionic acid.

Still another embodiment comprises a compound with the general formula:

z—o wherein O, for example, comprises an n-mer of the D-enantiomer of the amino acid arginine, or
pharmaceutically acceptable salt thereof, having for example the formula:

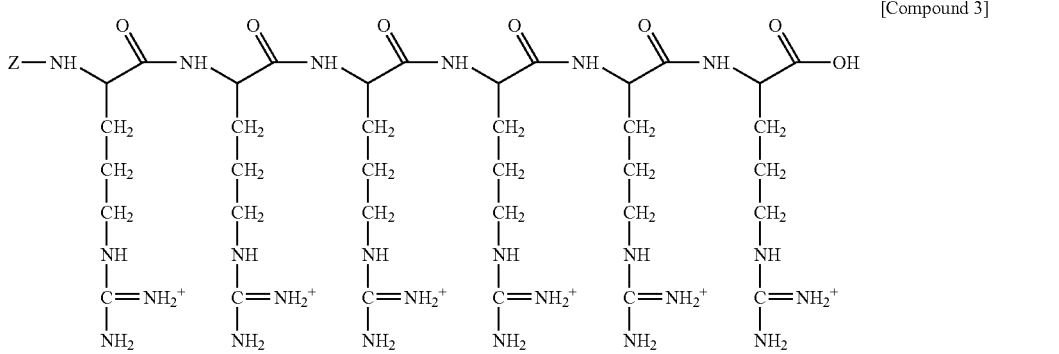

[Compound 3]

and

Z is hydrogen or an N-terminal blocking group, or the directing group α-lipoic acid, pyroglutamic acid, 4-morpholinylcaronyl, CBZ, or a propionic acid derivative, and z is bonded to the N-terminus of the terminal arginine Still another embodiment is a compound or pharmaceutically acceptable alt thereof, with the formula:

Z—U—C     [Compound 4]

wherein,

C is a group selected from the group comprising:

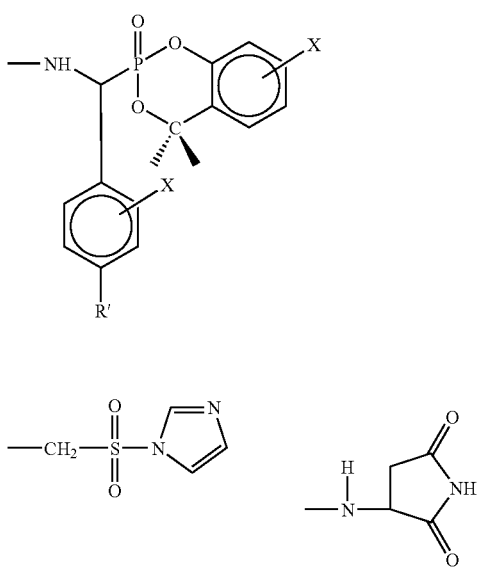

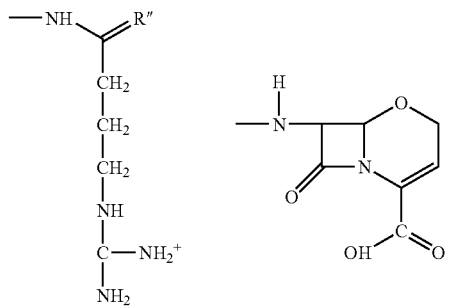

-continued

X is hydrogen (H) or fluorine (F);

U is a peptide with the general formula $(J)_n$-Arg in which $(J)_n$ is an n mer of amino acids joined together via peptide bonds, Q is at least one amino acid selected from the group consisting of Arg, Lys, Gln, Glu, Val, Ala, Phe, Thr, His, Ser, and Gly;

n is greater than or equal to 1 and less than or equal to 6;

Z is either hydrogen or an N-terminal blocking group selected from the groups comprising α-lipoic acid, pyroglutamic acid, 4-morpholinylcaronyl, CBZ, or a propionic acid derivative, Z is bonded to the N-terminus of the peptide U; and R' is selected from the group comprising:

hydrogen, fluorine and either

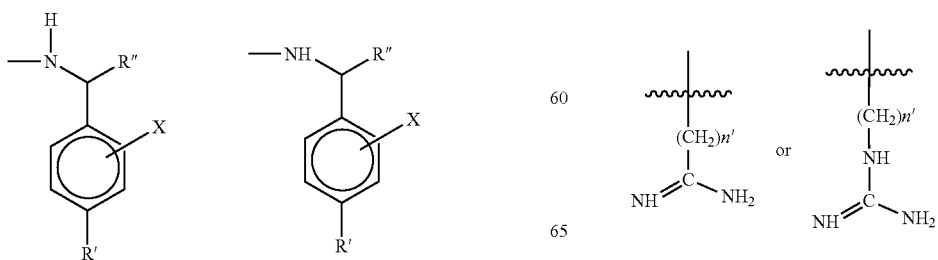

wherein n' is equal to or less than 4; and
R" is selected from the group comprising hydrogen, fluorine or
either

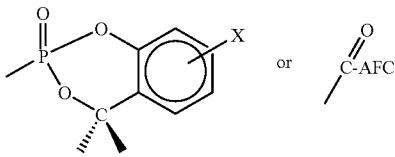 or 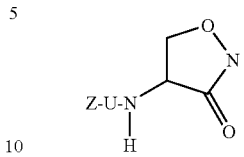

The N-terminal blocking group may be attached to either an amino acid or a peptide chain. In one embodiment the N-terminal blocking group is a group that has intrinsic anti-inflammatory activity, for example, 2-Acetoxybenzenecarboxylic acid. For a more complete listing of N-terminal blocking groups that can be used in various embodiments the reader is directed to Gilman, Goodman, Gilman, "The Pharmacological Basis of Therapeutics", Sixth Ed. MacMillian, Chapter 29, which is herein incorporated by reference in its entirety.

Yet another embodiment is the compound or a pharmaceutically acceptable salt thereof, with the following formula:

[Compound 5]

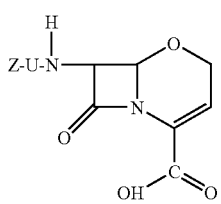

wherein,
U is a polypeptide with the general formula $(J)_n$-Arg in which $(J)_n$ is an n mer of amino acids joined together via peptide bonds, J is at least one amino acid from the group consisting of Arg, Lys, Gln, Glu, Val, Ala, Phe, Thr, His, Ser, and Gly; and
Z is selected from the group consisting of -lipoic acid, pyroglutamic acid, biotin, hydrogen, or fluorine, z is bonded to the N-terminus of the peptide U.

Another embodiment is the compound or pharmaceutically acceptable salt thereof, with the formula:

[Compound 6]

wherein,
U is a peptide with the general formula $(J)_n$-Arg in which $(J)_n$ is an n mer of amino acids joined together via peptide bonds, J is at least one amino acid from the group consisting of Arg, Lys, Gln, Glu, Val, Ala, Phe, Thr, His, Ser, and Gly, n is greater than or equal to 1 and less than or equal to 6; and
Z is selected from the group consisting of α-lipoic acid, pyroglutamic acid, biotin, hydrogen and fluorine and Z is bonded to the N-terminus of the peptide U.

Still another embodiment is the compound or pharmaceutically acceptable salt thereof, with the following formula:

[Compound 7]

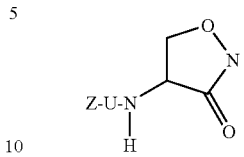

wherein,
U is a polypeptide with the general formula $(J)_n$-Arg in which $(J)_n$ is an n mer of amino acids joined together via peptide bonds, J is at least one amino acid from the group consisting of Arg, Lys, Gln, Glu, Val, Ala, Phe, Thr, His, Ser, and Gly, n is greater than or equal to 1 and less than or equal to 6; and
Z is selected from the group consisting of α-lipoic acid, pyroglutamic acid, biotin, hydrogen and fluorine.

Still another embodiment is the compound or pharmaceutically acceptable salt thereof, with the following formula:

[Compound 8]

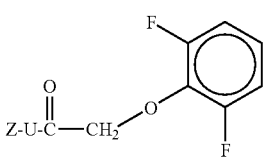

wherein,
U is a polypeptide with the general formula $(J)_n$-Arg in which $(J)_n$ is an n mer of amino acids joined together via peptide bonds, J is at least one amino acid from the group consisting of Arg, Lys, Gln, Glu, Val, Ala, Phe, Thr, His, Ser, and Gly, n is greater than or equal to 1 and less than or equal to 6; and
Z is selected from the group consisting of α-lipoic acid, pyroglutamic acid, biotin, hydrogen and fluorine, is bonded to the N-terminus of the peptide U.

Yet another embodiment is the compound or pharmaceutically acceptable salt thereof, with the following formula:

[Compound 9]

wherein,
U is a polypeptide with the general formula $(J)_n$-Arg in which $(J)_n$ is an n mer of amino acids joined together via peptide bonds, J is at least one amino acid from the group consisting of Arg, Lys, Gln, Glu, Val, Ala, Phe, Thr, His, Ser, and Gly, n is greater than or equal to 1 and less than or equal to 6; and
Z is selected from the group consisting of α-lipoic acid, pyroglutamic acid, biotin, hydrogen and fluorine, Z is bonded to the N-terminus of the peptide U;

R' is hydrogen, or fluorine, or

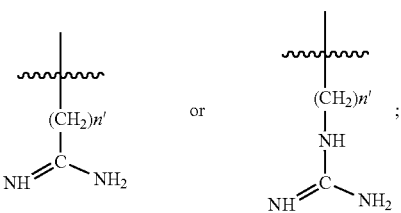

and A is selected from the group of amino-fluoro-acetic acid, OPh

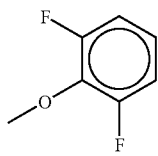

Another embodiment is the compound or pharmaceutically acceptable salt thereof, with the following formula:

[Compound 10]

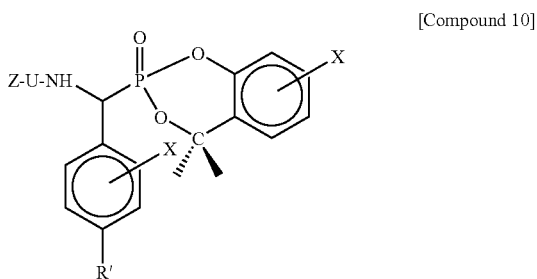

wherein,

U is a peptide with the general formula $(J)_n$-Arg in which $(J)_n$ is an n mer of amino acids joined together via peptide bonds, J is at least one amino acid selected from the group consisting of Arg, Lys, Gln, Glu, Val, Ala, Phe, Thr, His, Ser, and Gly, n is greater than or equal to 1 and less than or equal to 6; and;

Z is selected from the group consisting of α-lipoic acid, pyroglutamic acid, biotin, hydrogen and fluorine Z is selected from the group comprising α-lipoic acid, pyroglutamic acid, morpholino, $CB_2$, biotin, a lipoic acid, quinoly, groups and the like; Z is bonded to the N-terminus of peptide U; and R' is selected from the group comprising hydrogen, fluorine;

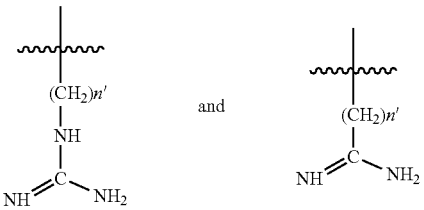

n' is greater than or equal to 0 and less than or equal to 4; and X is hydrogen, fluorine or a combination thereof.

In still another embodiment, therapeutically effective amounts of an appropriate furin inhibitor are administered in a therapeutic manner to a medical patient having a medical condition involving furin activity. Medical conditions involving furin activity include, but are not limited to, neuro-degenerative diseases, malignancies, and the like.

Medical conditions due to bacteria or viruses include, but are not limited to, infection with specific bacteria or viruses or exposure to various bacterial or viral toxins produced by any means. Means for producing diseases due to bacteria or viruses include exposure to bacterial or viral toxins produced through genetic manipulation or chemical synthesis.

Additional medical conditions that may be treated with furin inhibitors include exposure to virus or bacteria or viral or bacterial derived toxins before a human or animal patient becomes symptomatic for exposure to the pathogen.

In still another embodiment, appropriate furin inhibitors may be used to diagnose disease involving furin activity.

In yet other embodiments, appropriate furin inhibitors may be used to study furin activity as well as pathologies and components of pathology that involve furin activity.

BRIEF DESCRIPTION OF THE FIGURES

FIG. 6(*b*) is a photomicrograph (100× magnification) of type A-7 cells, inoculated with vaccinia virus and grown in vitro.

FIG. 6(*c*) is a photomicrograph (100× magnification) of type A-7 cells, inoculated with vaccinia virus and grown in vitro in the presence of 5 μM of one of the compounds, made in accordance with one embodiment.

FIG. 6(*d*) is a photomicrograph (100× magnification) of type A-7 cells, inoculated with vaccinia virus and grown in vitro in the presence of 25 μM of one of the compounds made in accordance with one embodiment.

FIG. 6(*e*) is a photomicrograph (100× magnification) of type A-7 cells, inoculated with vaccinia virus and grown in vitro in the presence of 50 μM of one of the compounds made in accordance with one of the embodiments.

FIG. 7(*b*) is a photomicrograph (100× magnification) of type A-7 cells, inoculated with vaccinia virus and grown in vitro.

FIG. 7(*c*) is a photomicrograph (100× magnification) of type A-7 cells, inoculated with vaccinia virus and grown in vitro in the presence of 5 μM of one of the compounds made in accordance with one of the embodiments.

DETAILED DESCRIPTION OF THE PREFERRED EMBODIMENTS

Figure 1:
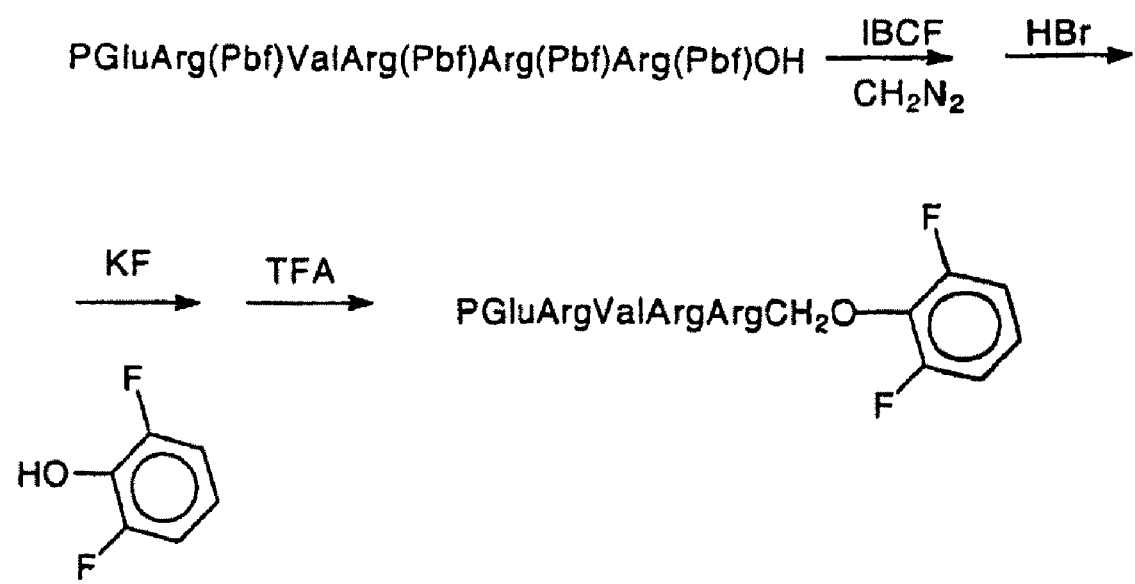
FIG. 1 is a schematic representation of the major steps in the synthesis of one compound according to one embodiment, which includes SEQ ID NO. 2.

For the purposes of promoting an understanding of the principles of the invention, reference will now be made to various embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

Furins are found in all vertebrates and are typically of about 794 amino-acid and characterized as a Type-1 transmembrane protein. Classified as a member of the protein convertase family it is also a member of the subtilisin superfamily of serine endoproteases. The active site of the enzyme rigorously conserves the Aspartic acid, Histidine, Serine (Asp, His, Ser) catalytic triad characteristic of proteases in the serine proteases superfamily. Typically, furin activity is calcium dependent and peaks over the pH range of 5-8 Standard Units (SA). By way of example and not of limitation, a sequence of one human form of a propeptide encoding a furin is presented in SEQ ID NO. 1. Again by way of illustration and not limitation, additional furins and molecules that include furin activity and can be used in conjunction with the present invention include those disclosed in U.S. Pat. No. 6,210,929 to Schlokat et al., issued on 3 Apr. 2001, U.S. Pat. No. 6,274,365 B1 to van de Ven et al., issued on Aug. 14, 2001, and International Publication WO/91/06314, published 16 May 1991, both of which are incorporated herein by reference in their entirety.

For further discussions of this polypeptide including a comparison of the furin and furin like proteins from various organisms, please see U.S. Pat. No. 6,271,365 B1, which is incorporated herein by referenced in its entirety.

The consensus proteolytic cleavage site for furin proteases is Arg-Xan-Xan-Arg, wherein Xan is preferentially a basic amino acids. For a more thorough discussion of furins the reader is directed to, "Proteolytic Processing of the Hepatitus B Virus e Antigen Precursor," Messagoet F., Salhi S., Eon, P., and Rossignol J., *Journal of Biological Chemistry* Vol. 278, Issue 2, 891-895 Jan. 10, 2003, incorporated herein by reference in its entirety.

Various embodiments of the invention relate to methods of treating medical conditions, characterized by the involvement of proteins processed by the protease furin. One embodiment provides for the treatment of pathologies caused by the over expression (or expression at inappropriate times) of a host encoded propeptides processed by furin.

The term peptide, as used herein, refers to a single amino acid joined to other groups via peptide or peptide like bonds. The term peptide also refers to short polypeptides, such as for example, amino acid residues that may or may not include both D and L enantiomers and are bonded to one another or to other groups by peptide or peptide like bonds.

Another embodiment provides for the treatment of medical conditions involving, or exacerbated by, furin processing of propeptides encoded by infectious agents. These infectious agents include microorganisms such as specific pathogenic protozoa and bacteria, as well as specific viruses.

A number of pathogenic organisms also produce proteins in proprotein form, which are processed into their mature, more active form by eukaryotic endoproteases. Because of its role in activating pathogen encoded propeptide, furin plays an essential role in the pathology of a number of infectious agents.

Examples of pathogenic bacteria that exploit furin activity to process their proproteins include *Psuedomonas areugenosa, Bacillus anthrasis*, and members of the genus *Clostridium* including *C. botulinum* and *C. tetani*. For a more exhaustive list see Table I.

Viruses, which exploit host furin activity for processing of viral encoded propeptides include, for example, Borna virus, Human Immunodeficiency Virus (HIV), Infectious Bronchitis virus, vaccinia virus, Hepatitus B, Ebola Zaire, Japan B Encephalitis virus, arboviruses (including the virus responsible for yellow fever), and Coronavirus (including the Coronavirus responsible for Severe Acute Respiratory Syndrome, SARS).

By way of illustration and not limitation, furin cleavage sites for some propeptides produced by some viral and bacterial pathogens are summarized in Table 1.

As used herein, amino acid residues may be designated as $P_1$, $P_2$, etc., wherein $P_1$ and $P_1'$ refer to groups nearest to and on opposite sides of the scissile bond, $P_2$ refers to the amino acid residue next to $P_1$ and nearer the blocking group, etc. For example, in a dipeptide inhibitor, $P_1$ is the amino acid nearest to the scissile bond cleared by the protease; if the N-terminal of the dipeptide is blocked the $P_1$ residue may be the group nearest to the blocking group.

As used herein, the one letter and three letter amino acid designations as are used in Table 1 and throughout the examples are those well-known in the art. For a specific reference, the reader is directed to see for example, Biochemistry, $2^{nd}$ ed., Lubert Stryer, W.H. Freeman & Co., 1975, pg. 16, herein incorporated by reference in its entirety.

TABLE 1

The furin cleavage site of selected bacterial and viral propeptides.

| Pathogen | P6 | P5 | P4 | P3 | P2 | P1 | P1' |
|---|---|---|---|---|---|---|---|
| *B. anthrasis* PA (SEQ ID NO. 3) | N | S | R | K | K | R | S |
| *Clostridium septicum* α toxin (SEQ ID NO. 4) | K | R | R | G | R | R | S |
| Diptheria toxin (SEQ ID NO. 5) | G | N | R | V | R | R | S |
| Proaerolysin (SEQ ID NO. 6) | K | V | R | R | A | R | S |
| *Pseudomonas exotoxin* A (SEQ ID NO.7) | R | H | R | Q | P | R | G |
| Shiga toxin (SEQ ID NO. 8) | A | S | R | V | A | R | M |
| Avian influenza HA (HSN-1) (SEQ ID NO. 9) | R | R | R | K | K | R | G |
| Borna disease virus (SEQ ID NO. 10) | L | K | R | R | R | R | D |
| Cytomegalovirus Gb (SEQ ID NO. 11) | T | H | R | T | R | R | S |
| Ebola Zaire (SEQ ID NO. 12) | G | R | R | T | R | R | E |
| Marburg (SEQ ID NO. 13) | V | Y | R | R | K | R | S |
| Epstein-Barr virus gB (SEQ ID NO. 14) | L | R | R | R | R | R | D |
| HIV gp160 (SEQ ID NO. 15) | V | Q | R | E | K | R | A |
| Infectious Bronchitis virus E2 (SEQ ID NO. 16) | T | R | R | F | R | R | S |
| Japan B encephalitis M (SEQ ID NO. 17) | S | K | R | S | R | R | S |
| Measles virus $F_o$ (SEQ ID NO. 18) | S | R | R | H | K | R | F |
| Mumps (SEQ ID NO. 19) | S | R | R | H | K | R | F |
| Respiratory-syncitial virus F (SEQ ID NO. 20) | K | K | R | K | R | R | F |
| Rous sarcoma virus env (SEQ ID NO. 21) | G | I | R | R | K | R | S |
| Yellow fever virus M (SEQ ID NO. 22) | S | K | R | S | R | R | S |
| Arbovirus[1] (SEQ ID NO. 23) | | | R | S | R | R | S |
| Coronavirus[2] (SEQ ID NO. 24) | | | R | K | R | R | S |
| Vaccinia virus (SEQ ID NO. 25) | G | I | R | A | R | R | S |

While many of the inhibitors are discussed in terms of molecules including between one and four amino acids in positions $P_1$ through $P_4$. The inclusion of additional groups can, in some instances, be used to further refine the binding affinity of the molecules. For example, in some instances, other amino acids or amino acid analogues in positions beyond $P_1$ through $P_6$ may be added to the molecule to modulate the binding affinity of the molecule in a given therapeutic or experimental setting.

Linking a furin inhibitor to the N-termini of the proteolytic cleavage site, for the example, the N-terminus of an amino acid in the $P_4$ position can affect the biophysical and biochemical properties of the molecule. Such N-terminal groups can, for example, help direct the furin inhibitors to specific regions of the cell, for example, to the Golgi apparatus or the membrane.

These types of directing groups are useful when the furin inhibitors are used in vivo and they are especially useful when it is desirable to differentially inhibit furin activity either on the cell surface or in the Golgi apparatus. Useful directing groups for the practice of the instant invention include, but are not limited to, α lipoic acid, pyroglutamic acid and certain D-amino acids.

One aspect of the invention provides furin inhibitors that are particularly effective in both in vivo and in vitro applications.

Leaving groups that may be used in various embodiments include, for example, OPH In various embodiments, a number of different leaving groups and a number of different amino acid recognition sites have been named. Furin activity is an essential component of virtually all healthy host cells. Accordingly, broadly inhibiting furin activity is not necessarily desirous in all therapeutic settings. To that end, a number of different leading groups and a number of different recognition sites have been provided. One strategy for the use of such substrate recognition sites and leading groups is to tailor a specific therapeutic compound to treat a specific pathogenic state. For example, in order to treat an infection caused by bacteria, which relies upon host furin processing of a bacterial encoded proprotein, it may not be necessary or desirous in all situations to provide a furin inhibitor that effectively competes with the furin's native substrate. It may be more effective to provide a furin inhibitor that has a higher affinity for a furin-active site than does the bacteria proprotein. And at the same time, a lower affinity for the furin active site than does propeptides encoded by the host. The appropriate choice of substrate recognition site can be used to limit collateral damage otherwise done to the host cell by blanket inhibition of host furin activity.

Similarly, it is possible to select an appropriate leading (directing group) to cause an accumulation of furin inhibitor where it will have the greatest therapeutic impact. Conversely, it may be possible to use the directing group to steer the bulk of the inhibitor away from areas of the cell where the inhibitor is most likely to cause adverse side effects and little therapeutic gain.

For example, judicious use of the proper substrate recognition sites and directing groups in conjunction with the inhibitors and the other compounds of various embodiments of the invention can be used to selectively prevent or treat various infections and other pathogenic states with a minimum of adverse side effects.

One embodiment provides compounds and methods for the prevention, diagnosis, and treatment of diseases caused by bacteria that exploit host furin activity. Bacteria that exploit host furin activity include, but are not limited to, *Psuedomonas areugenosa, Corynebacterium diptheriae, Bacillus anthrasis*, and members of the genus *Clostridiu*, including, for example, *C. botulinum* and *C. tetani*.

One embodiment provides compounds and methods for the prevention, diagnosis, and treatment of diseases caused by viruses that exploit host furin activity. Viruses that exploit host furin activity include, but are not limited to, Borna virus, Human Immunodeficiency Virus (HIV), Infectious Bronchitis virus, Ebola Zaire, Japan B Encephalitis virus, arboviruses including, for example, the virus responsible for Yellow Fever, and Coronaviruses including the Coronavirus responsible for Severe Acute Respiratory Syndrome (SARS).

Still another embodiment provides compounds and methods for treating, preventing, and diagnosing human and animal diseases that involve pathogenic expression of native proproteins processed by furin. These conditions include, but are not limited to, degenerative joint diseases (such as rheumatoid arthritis), various forms of dementia including, but not limited to, Alzheimer's disease, familial British dementia (FBD) and familial Danish dementia (FDD), and tumor metastasis. Other pathologies that may be treated using these furin inhibitors include, for example, non-small-cell lung carcinomas, squamous-cell carcinomas of the head and neck, and Glioblastomas.

By way of explanation and not limitation, it is also to be appreciated that during the course of the reaction of the enzyme with some of the inhibitors, the carbonyl of the inhibitor is thought to rehybridize to $sp^3$ and to form a ketal intermediate with the thiol functionability of the enzyme. When the reaction between some of the inhibitors and the enzyme occurs under acidic conditions, other ketals can exchange with this intermediate either by going through the ketone or by ketal-ketal exchange. Accordingly, ketals can be substituted for carbonyls in the peptidyl inhibitors of the present invention. Similarly, other compounds such as hydrazones, hemiketals, oximes, imines, cyanohydrins, enolethers, enamines, hemithioketals, and the like are to be considered carbonyl equivalents and may be substituted for a carbonyl (or to give a carbonyl) under the acidic conditions of these inhibition reactions. Utilization of such derivatives can also be vehicles to either improve the bioavailability of the inhibitor drug or keep it from crossing a cellular membrane depending upon the hydrophobic nature of the masking function.

It is also to be appreciated that the development and synthesis of compounds having isosteric replacements of amide bonds is now a standard practice in the development of biologically active peptides once the optimum peptide sequence has been identified. Accordingly, one aspect of the present invention includes compounds having one or more modified amide bonds in the peptide sequence so long as conformation and binding are maintained while secondary enzymatic hydrolysis is prevented. For a list of such modifications, see for example, Kaltenbronn, 33, *J. Med. Chem.*, 838. In addition, inhibitors having a hydrazine replacement for the $P_1$ nitrogen as reported by Giordano for other halogen methyl ketones are also intended to be claimed.

Some embodiments relate to inhibiting furin processing of proproteins (propeptides) in humans, animals, and in organs, tissues, or cells maintained in culture by administering effective amounts of an inhibitor of the endoprotease.

Still other embodiments involve methods of treating diseases involving furin endoprotease activity by administering to a human, or an animal, patient therapeutically effective amounts of a furin inhibitor in a suitable drug delivery vehicle.

Yet another embodiment provides methods of treating diseases involving furin endoprotease activity, and/or serine protease activity by administering to a human patient or animal a therapeutically effective dose of a furin inhibitor in a suitable drug delivery vehicle.

One embodiment is a method of diagnosing disease in humans or animals using an assay comprising a furin inhibitor as, for example, a reagent.

The various compounds disclosed herein in various embodiments may be prepared for administration to both human and animal patients as appropriate for each compound and therapeutic or prophylactic situation by methods well known in the pharmaceutical art. If administered as a solid, the compounds may be mixed with a carrier or excipient. The specific carrier or excipient used may be a solid, semi-solid, or liquid material that can serve as a vehicle or medium for the active ingredient. Suitable carriers or excipients are well known in the art. The pharmaceutical composition may be adapted for intravenous, oral, inhalation, parenteral, or topical use and may be administered to the patient in the form of tablets, capsules, aerosols, inhalants, suppositories, solutions, suspensions, or the like.

The compounds of the present invention may be administered intravenously, for example, as aqueous solutions including suitable carriers. Suitable carriers are well known to the art and include ethanol, Tween-80, solutol, Cremophor and the like.

The compounds of the present invention may also be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. The actual amount of the compounds in such preparations but may be varied depending upon the particular form and therapeutic application and dosing strategy. The amount of the compound present in compositions is such that a suitable dosage will be obtained. Preferred compositions and preparations of the present invention may be determined by methods well known in the art.

Tablets, pills, capsules, troches, and the like may also contain one or more of the following adjuvants: binders such as povidone, hydroxypropyl cellulose, microcrystalline cellulose, gelatin and the like; excipients or diluents such as: starch, lactose, microcrystalline cellulose, dicalcium phosphate and the like, disintegrating agents such as: croscarmellose, crospovidone, sodium starch glycolate, corn starch and the like; lubricants such as: magnesium stearate, steric acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol, oils or the like. Other dosage unit forms may contain other various materials that modify the physical form of the dosage unit, for example, as coatings.

Accordingly, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

The compounds of the present invention may also be administered in the form or an aerosol, mist, vapor or the like. When administered, as for example an aerosol, the compounds present in a therapeutically significant amount may be combined with any non-toxic non-cross reacting carrier as is known in the art.

EXAMPLES

The following examples are included by way of illustration and not limitation. All of the reagents use in the following examples are preferable reagent grade or better.

Where used, primarily in the synthesis examples, the amines, amino cepham acid, cycloserine and cyclic aspartic imide were all purchased from Acme Biosciences, Belmont, Calif.

Where used the reagent dihydrochloride was prepared in accordance with the method of Jozef Oleksyszyn as pub-

Example 1

Referring now to FIG. 1, the synthesis of PGluArgValArgArgOPH (SEQ ID NO. 27). 100 mg. (1.0 equivalents) of PgluArg(Pbf)ValARg(Pbf)Arg(PBf)OH was dissolved in THf and cooled to −15° C. 0.01 ml (1.3 equivalents) of NMM was added to the cooled mixture followed by 0.01 ml (1.1 equivalents) of IBCF. The mixture was stirred for 20 minutes. Diazomethane, freshly made from diazald was added to the mixture and the reaction was stirred for one hour at −10° C. and then for 20 hours at room temperature. Next the solvent was removed and the residue purified by a single preparative TLC plate. The product eluted from the TLC plate in a solution of 9% MeOH in $CH_2Cl_2$. The reaction yielded 60 mg of diazomethyl ketone.

The diazomethyl ketone (60 mg, 1.0 equivalent) was dissolved in THF:Ether:$CH_2Cl_2$ (2:2:2) and cooled to 0° C. 0.01 ml (1.2 equivalents) of HBr/HOAc as added to the mixture. The mixture was stirred for 30 minutes. After 30 minutes the solvent was removed and the residue was dried using a vacuum pump. The dried residue was dissolved in 3 ml of DMF comprising 1.0 equivalents of bromide, 6 mg (2.5 equivalents) of potassium fluoride and 5 mg (1.0 equivalents) of 2,6-difluorophenol and the mixture was stirred overnight.

Next, 50 ml of Ethyl acetate was added. The organic layer was washed with a saturated solution of NaCl and dried over $MgSO_4$. The solvent was removed and the residue was purified using a single preparative TLC plate. The intermediate eluted from the plate in a mixture of 9% MeOh in $CH_2Cl_2$ to give the protected difluorophenyl methyl ketone.

To remove the protecting groups, 95% TFA was added to the ketone and the mixture was stirred for 45 minutes. The solvent was removed and the residue was tritulated with ether to give the final product: PGluArgValArgArgOPH. The product had a molecular weight of 821 Daltons as determined my mass spectrometry. The reaction yielded was 30 mg of the named product.

Example 2

Figure 2:
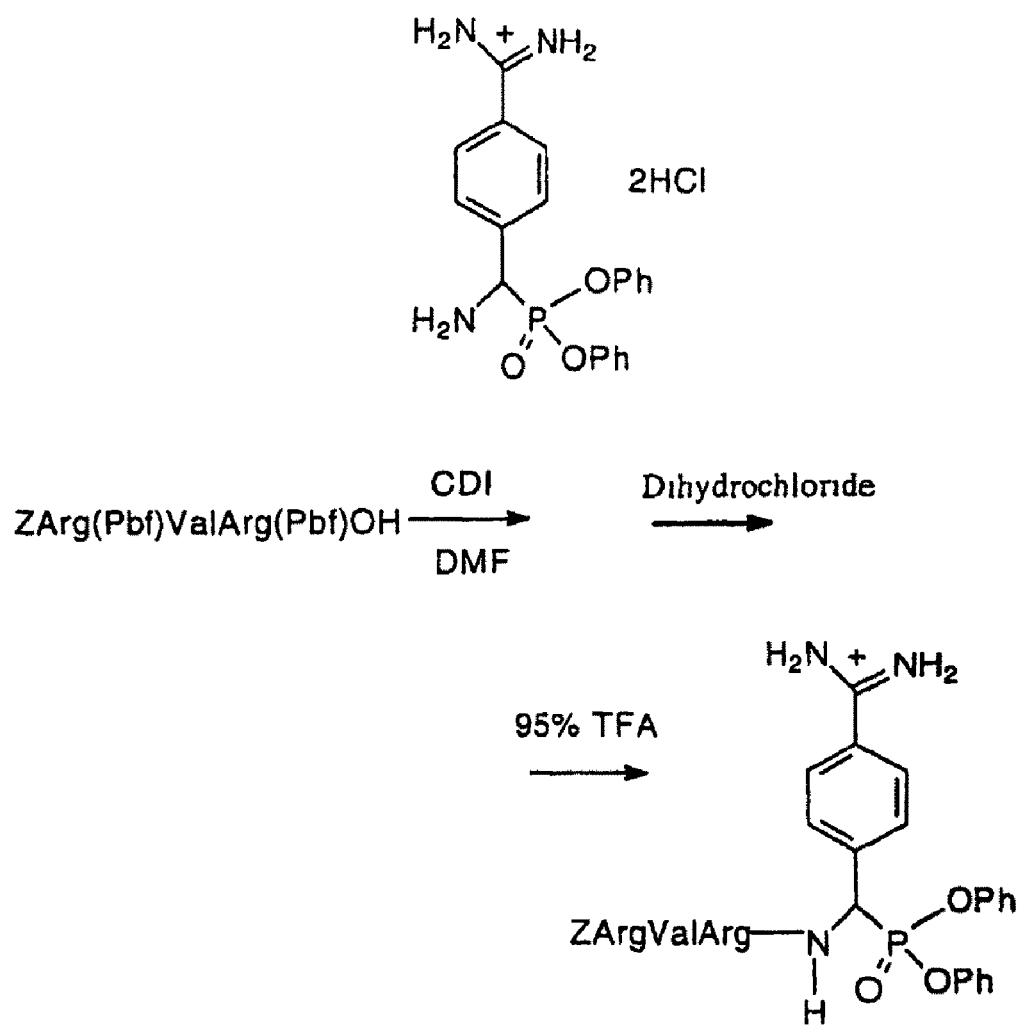
FIG. 2 is a schematic representation of the major steps in the synthesis of one of the compounds according to an embodiment of the present invention.

Synthesis of ZArgValArg(4-AmPhGly)(OPh)$_2$. Referring now to FIG. 2, 1.05 equivalents of DCI was added to 3 ml of DMF comprising 1.0 equivalents of ZArg(Pbf)ValArg)Pbf)OH at room temperature. The mixture was stirred for one hour then 1.0 equivalent of dihydrochloride was added followed by 1.0 equivalents of triethylamine. The mixture was stirred for two days.

After two days of stirring, 5 ml of a saturated solution of $NaHCO_3$ was added and the solution was extracted with two, 20 ml washes of ethyl acetate. The organic layer was washed with a saturated solution of NaCl and dried over $MgSO_4$. The solvent was removed and the residue was purified using preparative TLC. The reaction yielded protected phosphonate.

Next, 95% TFA was added to the protected phosphonate and the mixture was stirred for 45 minutes. The solvent was removed and the residue was tritulated with ether to give the titled product. The molecular weight of the product was 927 Dalton as determined my Matrix Assisted Laser Desportion Ion Spectroscopy (MALDI) mass spectrometry.

Example 3

The synthesis of X-ArgValArgArgArgCH$_2$Y, X is either alpha lipoic acid or proparglycine and Y is a specific amine.

Figure 3:
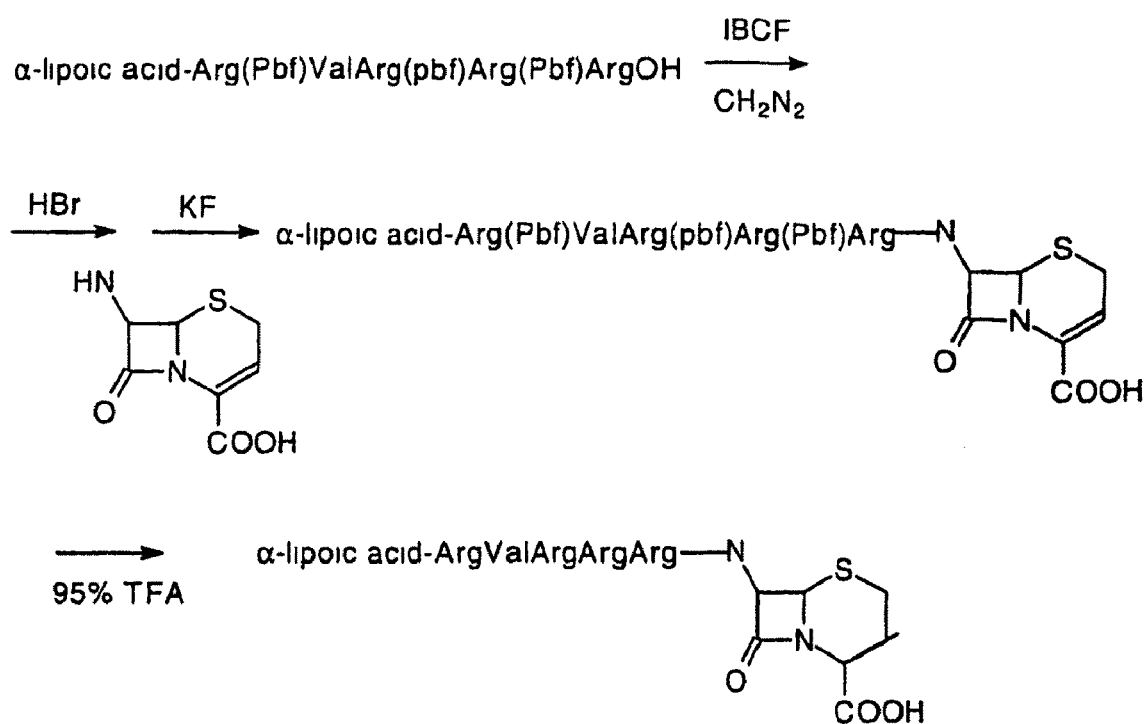
FIG. 3 is a schematic representation of the major steps in the synthesis of one of the compound according to one embodiment, which includes SEQ ID NO. 3.

Referring now to FIG. 3, 100 mg (1 equivalent) of α-lipoicAcid-Arg(Pbf)ValArg(Pbf)Arg(Pbf)Arg(Pbf)OH was dissolved in THF and cooled to −15° C. 0.01 ml (1.3 equivalents) of NMM was added to the cooled mixture followed by 0.01 ml (1.1 equivalents) of IBCF. The mixture was stirred for 20 minutes. Diazomethane, freshly made from diazald, was added to the mixture and the reaction was stirred for one hour at −10° C. and then for 20 hours at room temperature. Next, the solvent was removed and the residue purified by a single preparative TLC plate. The product eluted from the TLC plate in a solution of 9% MeOH in $CH_2Cl_2$. The reaction yielded 60 mg of diazomethyl ketone.

The diazomethyl ketone (60 mg, 1.0 equivalent) was dissolved in THF:Ether:$CH_2Cl_2$ (2:2:2) and cooled to 0° C. then 0.01 ml (1.2 equivalents) of HBr/HOAc as added to the mixture and the mixture was stirred for 30 minutes. After 30 minutes, the solvent was removed and the residue was dried under a vacuum. The dried residue was dissolved in 3 ml of DMF, that included 1.0 equivalents of bromide, 6 mg (2.5 equivalents) of potassium fluoride and 5 mg (1.0 equivalents) of 2,6-difluorophenol, and the mixture was stirred overnight.

Next, 50 ml of Ethyl acetate was added, and the organic layer was washed with a saturated solution of NaCl and dried over $MgSO_4$. The solvent was removed and the residue was purified using a single preparative TLC plate. The intermediate eluted from the plate in mixture of 9% MeOh in $CH_2Cl_2$ to give the protected difluorophenyl methyl ketone.

To remove the protecting groups, 95% TFA was added to the ketone and the mixture was stirred for 45 minutes. The solvent was removed and the residue was tritulated with ether to give the compound illustrated in FIG. 3.

Example 4

Figure 4:
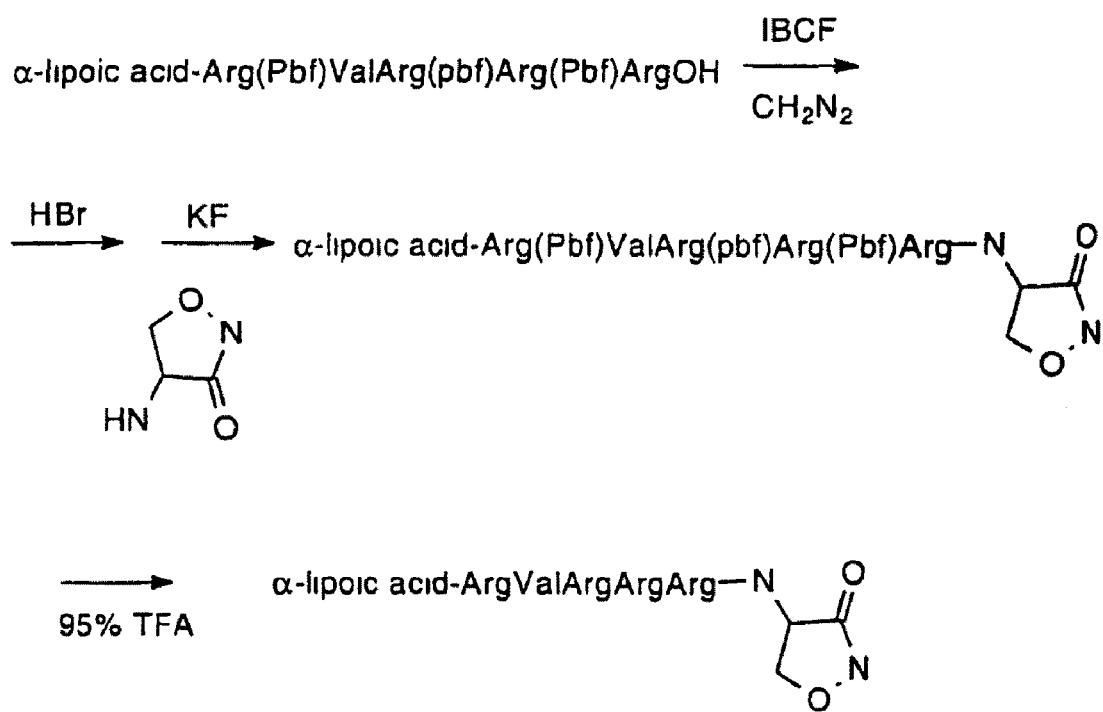
FIG. 4 is a schematic representation of the major steps in the synthesis of one compound according to one embodiment, which includes SEQ ID NO. 3.

Referring now to FIG. 4, the compound illustrated in FIG. 4 was synthesized by substantially the same method presented in Example 3. The only major difference was in the choice of amine.

Example 5

Figure 5:
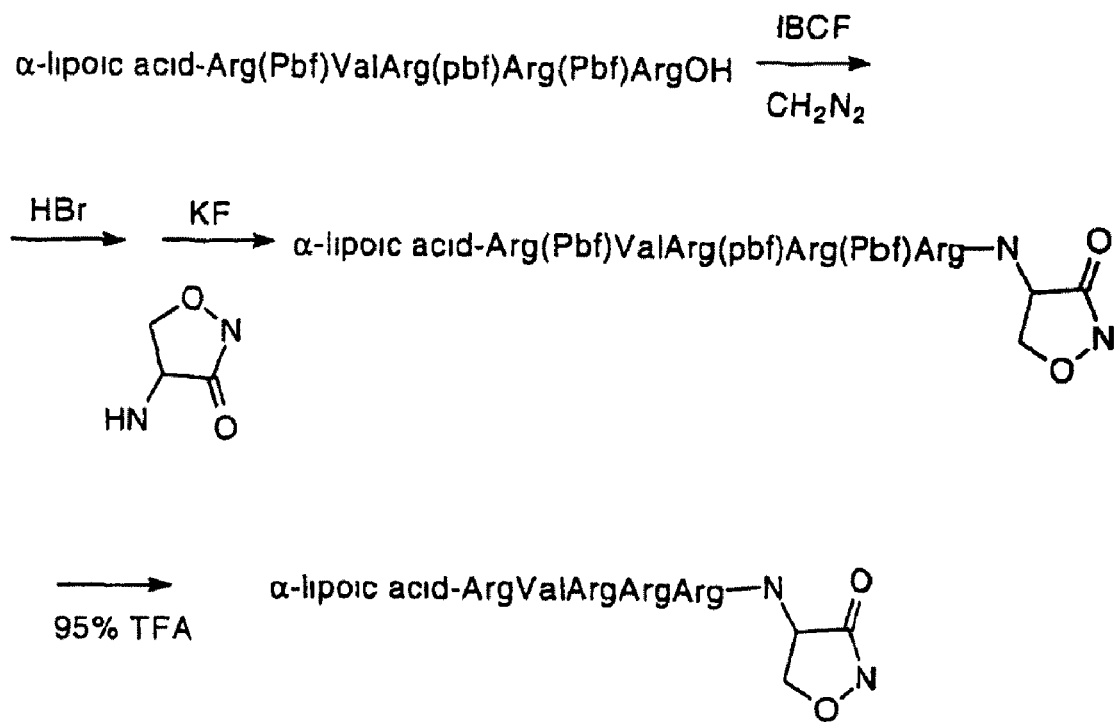
FIG. 5 is a schematic representation of the major steps in the synthesis of one compound according to one embodiment, which includes, SEQ ID NO. 3.
Figure 6A:
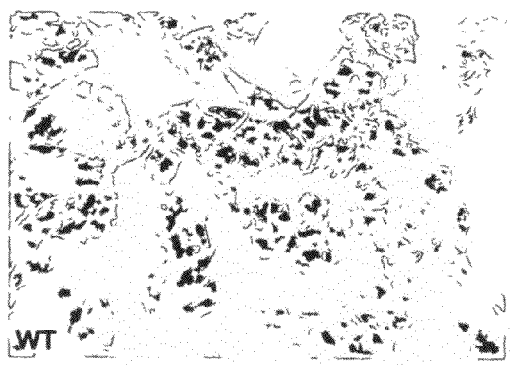
FIG. 6(*a*) is a photomicrograph (100× magnification) of wild type A-7 cells grown in vitro in the absence of either furin inhibitor or vaccinia virus.
Figure 6B:
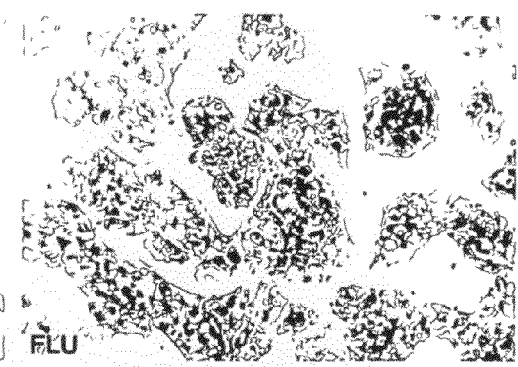
Figure 6C:
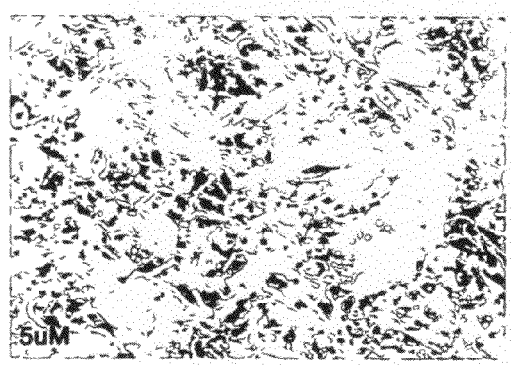
Figure 6D:
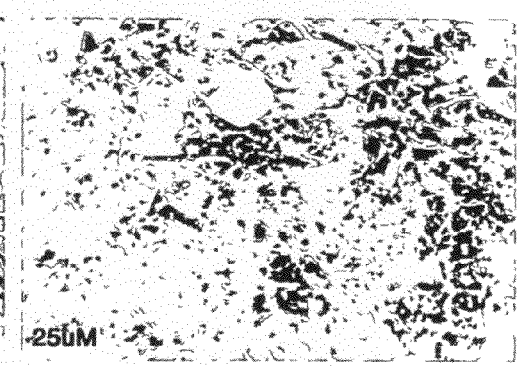
Figure 6E:
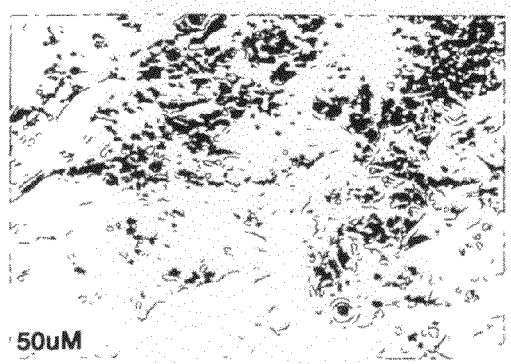
Figure 7A:
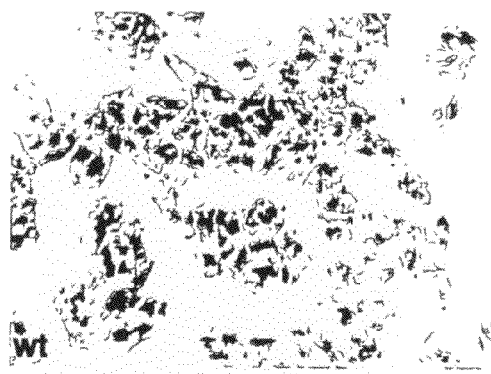
FIG. 7(*a*) is a photomicrograph (100× magnification) of wild type A-7 cells grown in vitro in the absence of either a furin inhibitor or vaccinia virus.
FIG. 7(d) is a photomicrograph (100× magnification) of type A-7 cells, inoculated with vaccinia virus and grown in vitro in the presence of 25 μM of one of the compounds made in accordance with one of the embodiments.
FIG. 7(e) is a photomicrograph (100× magnification) of type A-7 cells, inoculated with vaccinia virus and grown in vitro in the presence of 50 μM of one of the compounds made in accordance with one of the embodiments.
Figure 7B:
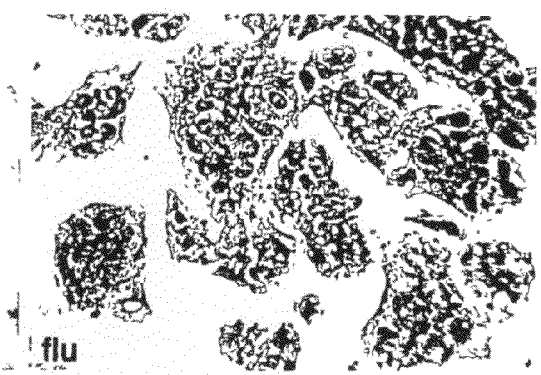
Figure 7C:
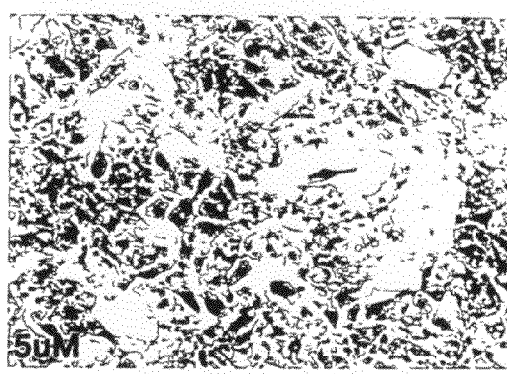
Figure 7D:
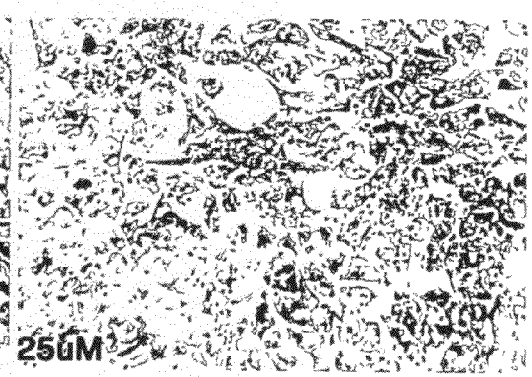
Figure 7E:
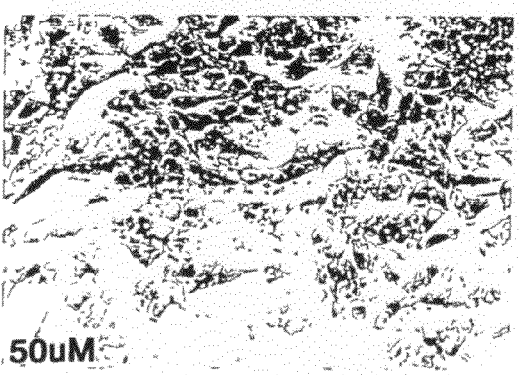
Figure 8A:
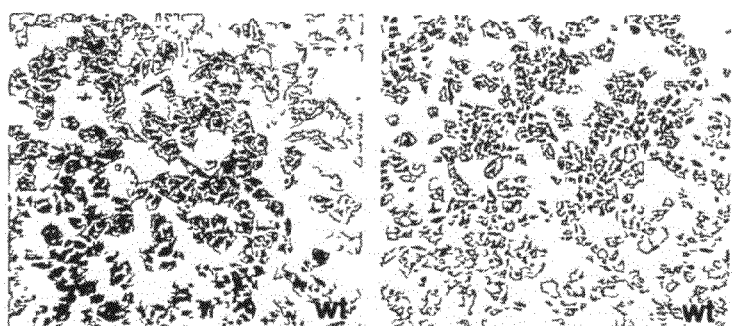
FIG. 8(a) is side by side photomicrographs (100× magnification) illustrating the results of two separate assays of wild type A-7 cells grown in vitro in the absence of either furin inhibitor or vaccinia virus.
Figure 8B:
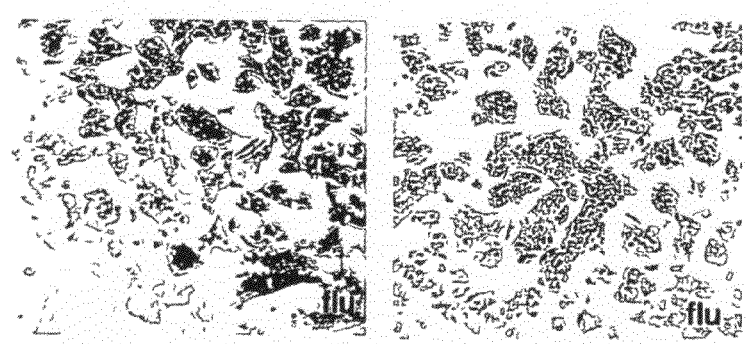
FIG. 8(b) is side by side photomicrographs (100× magnification) illustrating the results of two separate assays of type A-7 cells, inoculated with vaccinia virus and grown in vitro.
Figure 8C:
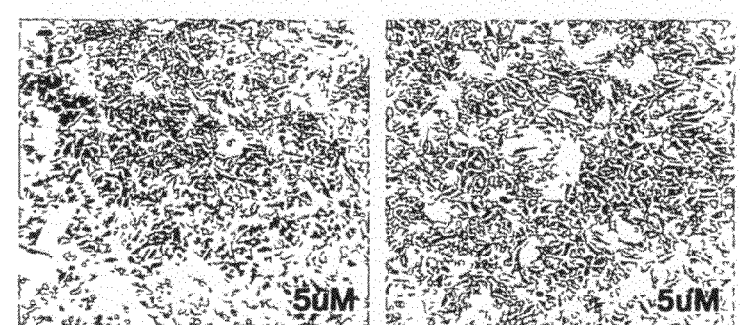
FIG. 8(c) is side by side photomicrographs (100× magnification) illustrating the results of two separate assays of type A-7 cells, inoculated with vaccinia virus and grown in vitro in the presence of 5 μM of one of the compounds made in accordance with one of the embodiments.
Figure 8D:
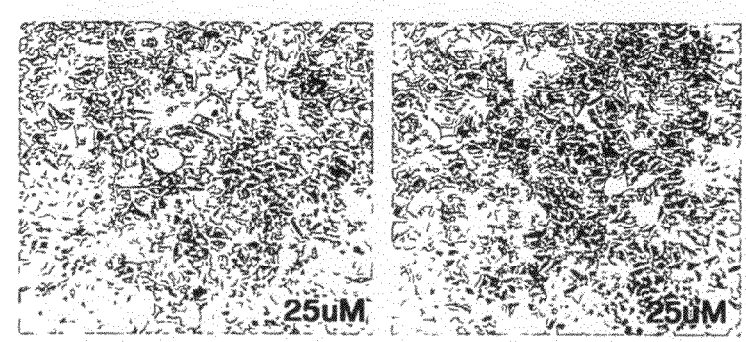
FIG. 8(d) is side by side photomicrographs (100× magnification) illustrating the results of two separate assays of type A-7 cells, inoculated with vaccinia virus and grown in vitro in the presence of 25 μM of one of the compounds made in accordance with one of the embodiments.
Figure 8E:
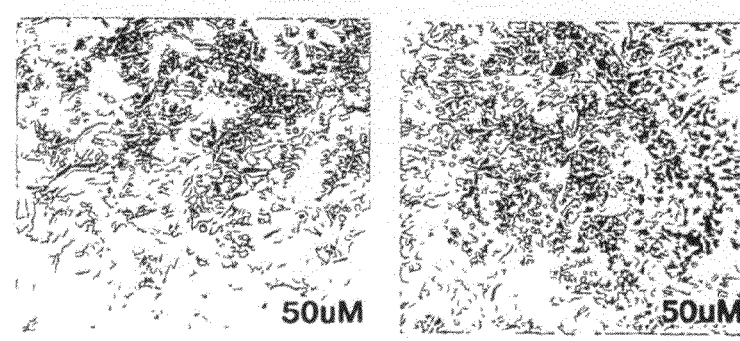
FIG. 8(e) is side by side photomicrographs (100× magnification) illustrating the results of two separate assays of type A-7 cells, inoculated with vaccinia virus and grown in vitro in the presence of 50 μM of one of the compounds made in accordance with one of the embodiments.

Referring now to FIG. 5, the compound illustrated in FIG. 5 was synthesized by substantially the same method presented in Example 3. The only major difference was in the choice of amine.

Example 6

Determining the prophylactic effect of some furin inhibitors, therapeutically effective amounts of compounds according to the formula of Compound 4 are administered to a group of genetically identical mice. As a control, a group of identical mice are maintained under identical conditions, and are not administered a therapeutically effective amount of Compound 4. Both sets of mice are challenged with an infectious amount of *Bacillus anthrasis*.

The two groups of mice, maintained under identical conditions, are followed for a period of ten days, and the mortality of the two groups is assessed. The mice receiving a therapeutically effective dose of Compound 4 suffer fewer fatalities than the mice in the control group.

Example 7

Determining the effect of Compound 4 using the in vitro assay method described by Cameron (Cameron, A.; Apel, J.; Houghten, R. A.; and Lindberg, I., "Polyarginines are Potent Furin Inhibitors", J. Biol. Chem., Vol. 275, Issue 47, 36741-36749, Nov. 24, 2000 incorporated herein by reference in its entirety), human furin is over expressed and purified.

Truncated versions of the furin enzyme are produced using the dyhydropholate reductase amplification method to over express truncated furin. This cell line secretes approximately 8 micrograms of furin into the culture medium. Purity is assessed using SDS Page Gel Electrophoresis, and staining with Coomassie Blue dye.

The actual activity assay is carried out in vivo as follows. A series of furin inhibitors as given for example in Table 2 are synthesized and tested for inhibition against furin. The assay for furin activity is performed in pH 5 buffer using the P Ertkr-MCA. An assay for furin activity is performed at pH 7, in 100 millimolar HEPES at 5 millimolar $CaCl_2$ in 0.5% brig 35. All assays are performed at 37 degrees C. in 96 well plates. Fluororescne is measured using a fluorometer with an excitation wavelength of 380 nanometers and an emission wavelength of 460 nanometers. The total assay volume is on the order of 50 microliters.

The final substrate concentration for all assays is about 200 micromoler. In some of the samples, furin is pre-incubated with furin inhibitor for 30 minutes at room temperature prior to the addition of the substrate molecule. Assays are performed in duplicate or triplicate. A number of compounds are tested as inhibitors of furin activity against a model substrate. Some of the compounds tested demonstrate varying degrees of concentration dependent inhibition of furin.

Example 8

The toxicity of various furin inhibitors disclosed in the embodiments of the invention is tested as follows. Various concentrations of inhibitor over a therapeutically effective range are administered to a series of mice over a period of time. The overall health of the mice is observed and assessed. Over a period of 10 days, various compounds used in the assay are not toxic at therapeutically effective concentrations used in the assay.

Example 9

One procedure for studying the efficacy of anti-tumor agents is to measure the inhibition of tumor growth and development in mice. See, for example, Corbett, et al., *In vivo Methods for Screening and Preclinical Testing; Use of rodent solid tumors for drug discovery*. In: Anticancer Drug Development Guide: Preclinical Screening, Clinical Trials, and Approval, B. Teicher (ed), Humana Press Inc., Totowa, N.J., Chapter 5, pages 75-99 (1997); Corbett, et al., *Int. J. Pharmacog.*, 33, Supplement, 102-122 (1995), incorporated herein by reference in its entirety.

Various compounds disclosed in various embodiments of the invention are tested for their ability to inhibit cancerous tumor growth in mammals such as mice. For example, murine tumors or human xenografts are implanted in mice essentially as described by Corbett in "*In vivo Methods for Screening and Preclinical Testing; Use of rodent solid tumors for drug discovery*" $2^{nd}$ Ed., Humana Press, 2004.

Briefly, the murine tumor or human xenograft is implanted subcutaneously using either 12-gauge trocar implants or counted number of cells. The location for the trocar insertion is midway between the auxiliary and inguinal region along the side of the mouse. The trocar is slipped approximately ¾ of an inch subcutaneously up toward the axilla before discharging the tumor fragment, and pinching the skin as the trocar is removed. Alternatively, human tumor cells can be prepared from a brie of donor tumors ($5 \times 10^6$ cells) and implanted subcutaneously in a hind-leg of a male or female nude mouse (Charles River). Either a test compound in vehicle or vehicle alone is administered by intravenous bolus injection (IV), intraperitoneal injection (ip), or oral gavage (po). Each treatment group, as well as a group of untreated control animals, consists of about five animals per group. Subcutaneous tumor response is monitored by tumor volume measurement performed twice weekly over the course of the experiment (60-120 days). Body weights are taken as a general measure of toxicity. The subcutaneous tumor data is analyzed by determining the median tumor weight for each treatment group over the course of the experiment and calculating the tumor growth delay as the difference in days for the treatment versus the control tumors to reach a volume of either 500 or 1000 $mm^3$.

Animals treated with compounds of the invention in the appropriate dosing range show a statistically significant reduction is healthier as assessed by body weight. Tumors in the treated animals are smaller than tumors in animals in the control group which receive only doses of same inert carrier used to prepare the therapeutic compounds of the invention.

Example 10

Tests were conducted to determine if a furin inhibitor with the same general formula as compound 8, in which $(R)_n$ is Arg-Arg-Arg was able to inhibit infection of A-7 cells with vaccinia virus in vitro.

A stock solution of the inhibitor with a concentration of 100 mM was made. A control, no inhibitor or viral inoculum (w. t.) and three test solutions were made. Next, additional inhibitor was added to cell media and incubated along with the cells for one hour at 37° C. at a final inhibitor concentration of 5, 25, or 50 µM, respectfully.

All cells except these in the wild type (w. t.) group were inoculated with 10 pfu/cell of Vaccinia virus (plaque forming material (pfm)). All cells, including those inoculated with vaccina, were incubated in PBS+ calcium buffer for 60 minutes at room temperature. Then the inoculum was removed from inoculated cells and all cells were fed with 2 ml of MEM supplemented with serum, and either with or without 5, 25, or 50 µM of the inhibitor.

The cells were then incubated for four hours at 37° C. Next, the cells were washed with serum free MEM and 1 ml of fresh PBS-M, pH 5.1 at 37° C. was added to the cells. The cells were allowed to sit for two minutes at 37° C. The cells were then quickly washed with 1×MEM supplemented with 10% serum. Next, the first wash was removed and 2 ml of fresh MEM supplemented with 10% serum either with or without the inhibitor was added. All cells were held at 37° C.

No Syncytia formed after 1 hour. A second pH 5.1 shock was performed on all of the cells and they were returned to the 37° C. environment. After another hour Syncytia formed. The samples were fixed in parafilm for 15 minutes and washed three times with PBS. The samples were stained with 1:10 methyl/crystal violet, and washed to remove excess stain. The samples were examined for evidence of viral infection under a Willovent tissue culture scope using a 10×-lens piece, giving a final magnifier of 100×. The experiment was run in duplicate. The samples were photographed and these photomicrographs are presented in FIGS. 6, 7 and 8.

FIGS. 6 and 7 are illustrative of separate experiments run under similar conditions. FIG. 8 is composed of images gathered from separate experiments displayed side by side. As illustrated in FIGS. 6, 7 and 8 *a* through *e*, separate distinct cells are visible in the wild type sample (not exposed to vaccina virus). The cell exposed to the flu virus in the absence of compound shows evidence of lysis. Cell membranes are compromised and multi-nucleated areas are clearly present. Referring now to FIGS. 6, c and d, cells provided with either 5 or 25 µM of the compound show multiple distinct cells. The cells are somewhat rounded and touching, but unlike the unprotected cells shown in FIG. 6b they are not generally lysed. Cell incubated with 50 µM also exhibited little evidence of cell lysis and merging, although vacuoles are clearly forming in some of the cells.

These results are consistent with low concentrations of the furin inhibitor protecting the cells from vaccina virus induced lysis. While higher concentrations of inhibitor protect from lysis by vaccina although the inhibitor may be somewhat toxic to the cells at high concentrations. As illustrated in FIG. 7, the tests were repeated and similar results observed at similar concentration of the inhibitor.

Example 11

Determination of the ability of the furin inhibitor with the general formula ERVRR-OPH to prevent components of the pathogenic pathway of bacillus anthracis from inhibiting protein synthesis in lung epethalial and macrophage cells. Briefly, anthrax toxin consists of three proteins lethal factor (LF) protective antigen (PA) and edema factor (EF). All three of these proteins working in concert are necessary to cause the death of an infected cell. In the course of infection PA is thought to bind to an AT receptor on the host cell surface, where PA is subsequently cleaved by furin (or a furin-like proteases) to produce two fragments. These two fragments are thought to consist of a 20 k-Da N-terminal fragment designated as $PA_{20}$ and a 63-K-Da C-terminal fragment designated as $PA_{63}$. For a more detailed discussion of this process, see Panchal, R. G. et al *Nature Structural and Molecular Biology*, Vol. 11 No. 1, page 67, January 2004, which is incorporated herein by reference in its entirety.

In order to test the efficacy of a furin inhibitor to interfere with the mechanism of anthrax toxicity, the following study was carried out. Cells in 12-well plates were incubated at 37° C. for two ours under one of the following three conditions: a) no putative prophylactic therapeutic, b) 100 µM Glu-Arg-Val-Arg-Arg-OPH or c) 100 µM decanoyl RVKR-CMK. Next all cells, except the cells in a control group, were exposed to 100 ng/ml of PA and 50 ng/ml of a fusion protein consisting of anthrax lethal factor and pseudomonas exotoxin (FP59).

After six hours all cells were rinsed with physiological buffer and pulsed with radioactive $^{35}S$ for 40 minutes followed by precipitation with Tri-chloro-acetic acid (TCA). Activity was accessed by scintillation counting. All assays were conducted in triplicate including the controls (cells not exposed to anthrax toxin). The amounts of protein biosynthesized were estimated by determining the amount of $^{35}S$ in the precipitates. Activity was accessed by scintillation counting. All values reported are normalized to the amount of radiolabeled protein in the control cells. The results are summarized in table II.

As indicated by the results summarized in Table II, both putative furin inhibitors used in the assay appeared to inhibit the ability of the anthrax toxin to affect protein biosynthesis.

TABLE II

Results of pulse chase assay for cell exposed to anthrax toxin in the presence and absence of putative furin protease inhibitors.

| Condition | Protein Synthesis Inferred From $^{35}S$ incorporation |
|---|---|
| Control cell (not exposed to Anthrax toxin) | 100 ± 15% |
| Cell exposed to Anthrax Toxin | 2.7 ± 0.4% |
| Cell exposed to Anthrax Toxin After Treatment with ERVRR-OPH (SEQ ID NO. 26) | 70.9 ± 8.7% |
| Cell exposed to Anthrax Toxin After Treatment with RVKR-CMK (SEQ ID NO. 27) | 86.9 ± 9.9% |

All references, patents, patent application and the like cited herein and not otherwise specifically incorporated by references in their entirety, are hereby incorporated by references in their entirety as if each were separately incorporated by reference in their entirety.

An abstract is included in to aid in searching the contents of the abstract are not intended to be read as explaining, summarizing or otherwise characterizing or limiting the invention in any way.

While the invention has been illustrated and described in detail, this is to be considered as illustrative, and not restrictive of the patent rights. The reader should understand that only the preferred embodiments have been presented and all changes and modifications that come within the spirit of the invention are included if the following claims or the legal equivalent of these claims.

The present invention contemplates modifications as would occur to those skilled in the art. It is also contemplated that processes embodied in the present invention can be altered, duplicated, combined, or added to other processes as would occur to those skilled in the art without departing from the spirit of the present invention. Unless specifically identified to the contrary, all terms used herein are used to include their normal and customary terminology in the art.

Further, any theory of operation, proof, or finding stated herein is meant to further enhance understanding of the present invention and is not intended to make the scope of the present invention dependent upon such theory, proof, or finding.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

It is understood that a number of variations may be made to adapt the present invention to a particular medical conditions, diagnostic test, experimental protocol, or the like without changing the basic compositions and methods disclosed herein. Therefore, while the invention has been illustrated and described in detail in the foregoing examples and discussion, the same are to be considered illustrative and not restrictive in character. The invention is in no way bound by any theory or explanation of how or why a particular feature of the invention functions.

The invention claimed is:
1. A compound having the following formula:
Z-0 or a pharmaceutically acceptable salt thereof, wherein 0 is the D-enantiomer of:
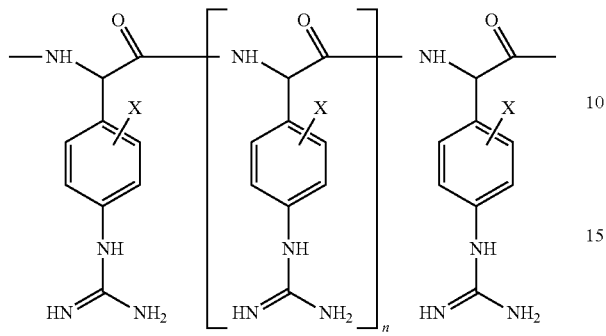
X is H, F, or a combination thereof;
n is 4 and
Z is independently selected from the group consisting of H, a-lipoic acid, pyroglutamic acid, 4-morpholinylcarbonyl, CBZ or propionic acid.
* * * * *